US006040153A

United States Patent [19]
Lemonnier

[11] Patent Number: 6,040,153
[45] Date of Patent: Mar. 21, 2000

[54] CARTRIDGE AS WELL AS AIR ANALYSIS METHOD AND APPARATUS USING IT

[75] Inventor: Jean Lemonnier, Paris, France

[73] Assignee: Millipore Corporation, Bedford, Mass.

[21] Appl. No.: 09/283,002

[22] Filed: Mar. 31, 1999

[30] Foreign Application Priority Data

Apr. 24, 1998 [FR] France ................................ 98 05 166

[51] Int. Cl.[7] ................................ C12Q 1/24; C12M 3/00

[52] U.S. Cl. ........................... 435/30; 435/34; 435/288.3; 435/305.1; 435/305.4; 435/309.1

[58] Field of Search ............................. 435/288.3, 288.4, 435/305.1, 305.4, 309.1, 30, 34; 73/863.21, 863.41, 863.53, 864.71

[56] References Cited

U.S. PATENT DOCUMENTS

| | | | |
|---|---|---|---|
| 3,338,794 | 8/1967 | Bladel | 195/126 |
| 3,684,660 | 8/1972 | Kereluk et al. | 195/139 |
| 3,886,047 | 5/1975 | Billups, Jr. | 195/139 |
| 3,922,905 | 12/1975 | Roth . | |
| 4,326,028 | 4/1982 | Brown | 435/32 |
| 4,912,037 | 3/1990 | Lemonnier | 435/34 |

FOREIGN PATENT DOCUMENTS

| | | |
|---|---|---|
| 0024048 | 8/1980 | European Pat. Off. . |
| 2732692 | 10/1996 | France . |
| 196 08 009 | 10/1997 | Germany . |
| 1441576 | 7/1976 | United Kingdom . |
| 2224118 | 4/1990 | United Kingdom . |

OTHER PUBLICATIONS

Search Report from the "Institut National de la Propriete Industrielle", French Application No. 9805166; dated Feb. 8, 1999; Examiner: A. Coucke (2 pages).

*Primary Examiner*—David A. Redding
*Attorney, Agent, or Firm*—John Dana Hubbard, Esq.; Timothy J. King, Esq.

[57] ABSTRACT

The cartridge has a body (2) with a grid (7) and an annular wall (8) oriented transversely to this grid and surrounding it, and having a layer (3) of growth media and a flexible fluid-tight film (4) tensioned over an end surface of the annular wall (8) and delimiting an end surface of the layer of growth media (3).

According to the method, the surface of the layer of growth media (3) delimited at the time of manufacture by the tensioned film (4) is struck with air jets in order to impact on this surface the microorganisms present in the air.

The apparatus has a positioning support common to a sieve for forming the air jets and to the body (2) of the cartridge (1).

20 Claims, 2 Drawing Sheets

CARTRIDGE AS WELL AS AIR ANALYSIS METHOD AND APPARATUS USING IT

The invention relates in general terms to the detection of microorganisms such as bacteria, yeast or molds. More particularly, it relates to a device for collecting, growing and detecting such organisms in an effective manner.

BACKGROUND OF THE INVENTION

It is known that, in order to effect this detection, receptacles are used containing a layer of growth media such as agar for receiving microorganisms coming from the environment which it is wished to monitor, the receptacle next being put to incubate at the required temperature and for the required time to enable the microorganisms received to develop in the form of colonies visible to the naked eye, so that they can be counted and identified.

The microorganisms are collected, according to the degree of accuracy sought, passively, for example with a petri dish that is left open for a few hours with the layer of growth media exposed to air in order to collect microorganisms by sedimentation, or actively, that is to say by depositing, under known conditions, microorganisms coming from a sample of predetermined volume of the medium which one wishes to monitor.

The invention aims to increase the accuracy of detection, in particular in the case of an active collection of microorganisms.

OBJECTS AND SUMMARY OF THE INVENTION

For this purpose it is proposed to use a cartridge for culturing microorganisms, having a body with a grid and an annular wall oriented transversely to said grid and surrounding it, and having a layer of growth media oriented parallel to said grid and coating it; characterized in that it has a flexible fluid-tight film tensioned over an end surface of said annular wall and delimiting an end surface of said layer of growth media.

This layer is placed in the cartridge by heating the growth media, such as agar in order to make it liquid and then running it into the bowl formed by the body and tensioned fluid-tight flexible film, from the side of the body which is opposite to that where the film is situated, a sufficient quantity of growth media being poured for the grid to be covered.

The end surface of the layer of growth media that is delimited by the film is intended to receive the microorganisms coming from the sample to be analyzed, the film of course being removed before depositing the microorganisms.

Compared with the prior cartridge described in French Patent 2605330, where it is a cover in fluid-tight contact with an end surface of the annular wall which delimits the layer of growth media, the present cartridge offers the advantage of benefiting from the excellent geometric precision which can be obtained from a tensioned film, and therefore to benefit from excellent reproducibility of the geometry of the surface of the layer of growth media delimited by the film.

The use of this surface for depositing the microorganisms coming from the sample makes it possible, by virtue of this reproducibility, to avoid there being, from one analysis to another, variations in the deposition conditions liable to affect the accuracy of the measurement.

In addition, this reproducibility considerably simplifies the task of the operator when the cartridge is used in an apparatus for microbiological analysis of air of the type where the air sample is drawn through a sieve having a multitude of calibrated holes so that a multitude of fine air jets strike one of the end surfaces of a layer of growth media so that the microorganisms present in the air sample are fixed on this layer of growth media.

As a matter of fact, the use of a cartridge as disclosed above, where the surface of the layer of growth media delimited at the time of manufacture by the flexible film serves as a surface struck by the fine air jets, makes it possible, because of the precision of the geometry of this surface, to avoid the step of adjusting the separation between the surface which is to be struck and the sieve, the simple fitting of the cartridge and sieve being sufficient to obtain the required characteristics for this separation.

It will be noted that the elimination of the separation adjustment increases the reliability of the results, since this adjustment was tricky and therefore a source of measurement errors. According to preferred features, the cartridge has a removable cover adapted to wedge the film between the external surface of said annular wall and an internal surface of a lateral wall of said cover.

The fitting of the cover onto the annular wall of the body where the film has previously been positioned affords a tensioning of the film because the internal surface of the lateral wall of the cover as it slides over the film beyond the end surface of the annular wall of the body and therefore tends to drive the film along the external surface of this annular wall, so that the film is automatically tensioned simply by lifting on the cover.

It will also be noted, in general terms, that the presence of the cover is favorable to the preservation of the layer of growth media since the cover maintains the tension in the film and offers it mechanical protection.

Preferably, said cover is also adapted to wedge said film between said end surface of said annular wall of the body and a second internal surface of said cover. The fact that the film is thus wedged at the end of the fitting-on movement, where it is tensioned, is favorable to the tightness between the film and the end surface of the annular wall of the body.

Preferably, said cover has a closure flange disposed at a distance from said film when said second internal surface of the lateral wall of the cover wedges said film against said end surface of said annular wall of the body.

Thus, after having removed the film and deposited the microorganisms on the end surface of the layer of growth media which the film initially delimited, the cover can be fitted on directly until it comes into abutment in order to proceed with the culturing of the microorganisms, the space required between the surface of the layer of growth media and the flange being provided directly, which is much more convenient than the aforementioned prior cartridge where special measures must be taken to enable this space to exist.

Preferably, said cover has at least one hole allowing communication between the inside and outside of the cover when the latter is fitted onto said body. This hole or holes enable the sterilization gas to enter at the time of manufacture, and permit the necessary gaseous exchanges between the inside and outside of the cover during culturing (aerobic or anaerobic).

Preferably, said body and said cover are each made from molded plastic material, said cover being more flexible than said body. The difference in hardness between the body and cover assists their cooperation and enable them to tension and wedge the film as well as possible.

According to other preferred features, notably for reasons of simplicity and convenience, said film is made from plastic.

According to other preferred features, the cartridge has a removable base adapted to fit onto said body opposite said film in order to delimit a fluid-tight chamber onto which gives the end surface of said layer of growth media which is opposite to the one delimited by said film.

This chamber, by virtue of its fluid-tight character, can be put to a pressure higher than the external pressure which is the one intended to prevail on the end surface of the layer of growth media initially delimited by the film. This higher pressure is favorable, as will be explained below, to the rehomogenisation or rehydration of the layer of growth media.

Preferably, for practical reasons of manufacture and convenience in obtaining fluid-tightness:

a. said base fits externally onto said annular wall of said body and has an internal surface coming into contact with the end surface of said annular wall situated on the same side as the base; and/or b. said body and said base are made from molded plastic, said base being more flexible than said body.

According to other preferred features said body has, between said annular wall and said grid, a solid annulus having towards the inside an extra thickness part forming a ridge. This ridge due to a higher thickness, because it is present towards the inside, remains coated by the layer of growth media, even when the latter has shrunk to a certain extent, which has had the effect of separating its periphery from the annular wall of the body.

Given that the ridge remains coated and the annulus is solid, there is no possible passage between the circumference of the layer of growth media and the body, so that the spaces situated inside the body respectively on each side of the layer of growth media are separated in a fluid-tight fashion. This makes possible the existence of the above-mentioned fluid-tight chamber.

Preferably, said annulus has no projection on the side facing the film. This absence of projection on the side opposite to the one through which the layer of growth media is poured enables the latter to be disposed correctly between the film and the annulus.

According to other preferred features, in order to facilitate the counting of the colonies once the culturing has been effected, said grid has square meshes, and optionally is in a color contrasting with said layer of growth media.

The invention also relates, in a second aspect, to an air analysis method characterized in that it includes the use of a cartridge as disclosed above, with a step of striking by air jets said end surface of the layer of growth media delimited initially by said film. As explained above, the precision obtained by the film of the cartridge according to the invention is particularly favorable to the simplicity and accuracy of the striking step. According to preferred features, the method according to the invention includes, after said striking step, a step of depositing a predetermined volume of rehydrating solution on the end surface of said layer of growth media opposite to that delimited initially by said film. The deposition of this solution rehydrates, through the layer of growth media, the end surface initially delimited by the film, that is to say the one which was struck, and therefore dried, by the airjets.

Preferably, said step of depositing a predetermined volume of rehydrating solution is performed with said cartridge turned over.

The rehydrating solution thus progresses through the layer of growth media by gravity. It should be noted, as explained below, that the rehomogenization and rehydration take place more rapidly when there is also a slight overpressure on the side of the layer of growth media where the rehydrating solution is deposited.

The invention also relates, in a third aspect, to an air analysis apparatus having a removable sieve with a wall in which there are formed a multitude of fine perforations each forming an air jet striking a surface of a layer of growth media in a receptacle fitted in said apparatus, characterized in that said receptacle is formed by a cartridge as disclosed above, the struck surface being the end surface of the layer of growth media initially delimited by said film, and in that said apparatus has a positioning support common to said sieve and to the body of said cartridge.

This common support, rather than distinct supports liable to have a variable relative positioning because of the manufacturing tolerances, makes it possible to have a precise and repeatable relative positioning of the sieve with respect to the body, and therefore of the sieve with respect to the surface of the layer of growth media initially delimited by the film, since it is on the body that the film is tensioned.

Preferably, for practical reasons of size and air circulation in the apparatus, the common support has notches for housing the end of external lugs on said body.

Preferably, said lugs are perforated, so that they interfere with the circulation of air towards the suction turbine as little as possible.

The disclosure of the invention will now be continued with the description of an example embodiment, given below for illustration purposes only and are not meant to be limiting with reference to the accompanying drawings.

IN THE DRAWINGS

DETAILED DESCRIPTION OF THE INVENTION

Figure 1:
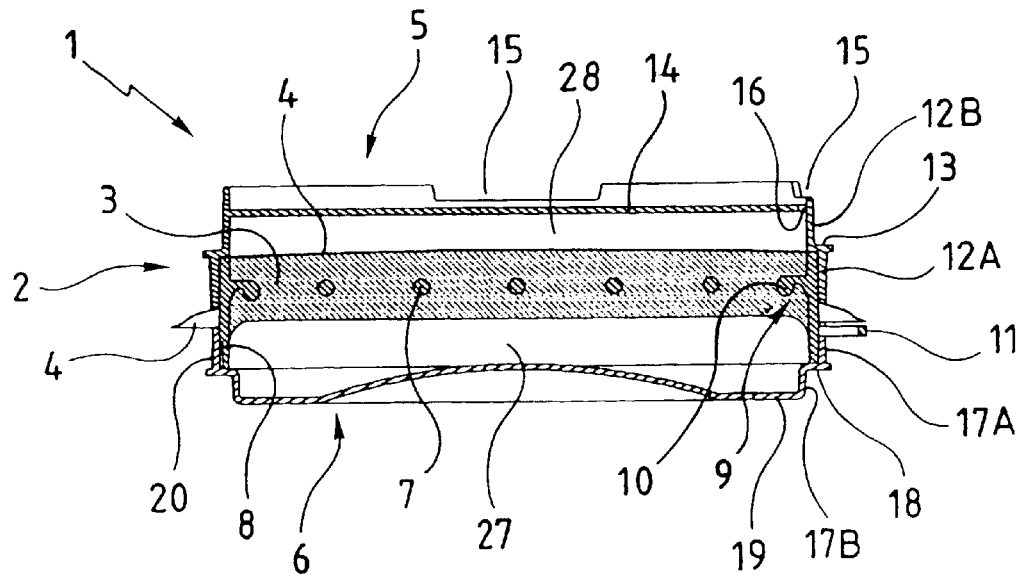
FIG. 1 is an elevation view in section through a cartridge according to the invention.

The illustrated cartridge 1 has a body 2, a layer of growth media 3, a film 4, a cover 5 and a base 6. The body 2 is made from relatively rigid molded plastic material. It has a grid 7 and an annular wall 8 oriented transversely to the grid 7 and surrounding it.

Figure 2:
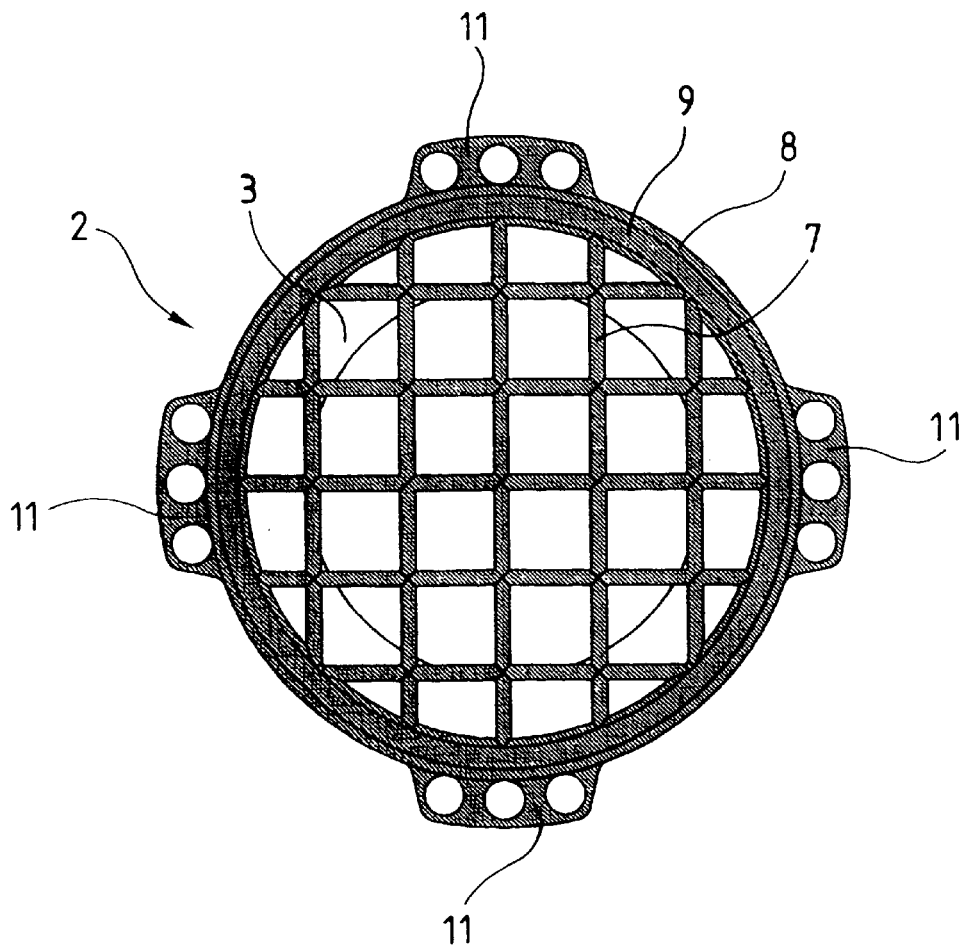
FIG. 2 is a plan view of this cartridge in which the cover, the film and the layer of growth media are not depicted.

The grid 7 as shown is formed by strands with a circular cross section, as can be seen notably in FIG. 1, and it has square meshes, that is to say with four sides each having the same length, as can be seen in FIG. 2.

The periphery of the grid 7 is connected to the wall 8 by means of a solid annulus 9 having towards the inside, that is to say towards the grid 7, an extra thickness part forming a ridge 10, the extra thickness here being present solely on the side which faces the base 6 (there is no projection on the side which faces the film 4).

The annular wall 8 has a constant thickness and has the general shape of a relatively short tube with a circular cross section. Between its end surface on the same side as the film 4 and the annulus 9, the wall 8 extends over a predetermined length corresponding substantially to half the thickness provided for the layer 3 of growth media, whilst it extends over a length approximately twice as great between the annulus 9 and its end surface situated on the same side as the base 6.

Projecting lugs 11 extend transversely from the external surface of the wall 8, the distance between the lugs 11 and the end surface of the wall 8 situated on the same side as the film 4 being precisely identical for each of the lugs. Perforations are formed in each of the lugs 11. The latter are here four in number, and each has three perforations. The film 4 is made from flexible fluid-tight plastic material. It is initially in the shape of a square with rounded corners, with sides appreciably longer than the diameter of the external surface of the wall 8. Once the cover has been installed, the corners of the film form protuberances that facilitate its gripping.

The cover 5 is made from semi-rigid molded plastic material, which is therefore more flexible than the material of the body 8. It has the general shape of a bowl, the lateral wall of which consists of two tubular parts with a circular cross section 12A and 12B and an annular part 13 oriented transversely to the parts 12A and 12B between which it is disposed.

The part 12A has an internal diameter which is very slightly greater than that of the external diameter of the wall 8, so that the part 12A can be fitted with a certain amount of gripping around the wall 8 with the film 4 interposed between this wall and the part 12A.

The part 12B has an internal diameter that is smaller than that of the part 12A, the internal surfaces of the parts 12A and 12B being connected by an annular surface provided by the part 13, the dimensions of this annular surface corresponding to those of the end surface of the wall 8 situated on the same side as the film 4, so that the latter can be applied closely to this end surface of the wall 8 when the cover 5 is pushed onto the body 8 until it comes into abutment.

The cover 5 is closed by a flange 14 formed by a flat wall connected by its periphery to the internal surface of the part 12B of the lateral wall, the flange 14 being oriented transversely to this part. The flange 14 is disposed at a relatively great distance from the end of the part 12B that is connected to the part 13. The part 12B has a portion situated between the flange 14 and its free end in which indentations 15 are formed. Four small holes 16 are formed in the flange 14 at its junction with the part 12B of the lateral wall respectively level with the center of each of the indentations 15. The base 6 is made from semi-rigid molded plastic material, just as the cover 5. Like it, it has the general shape of a bowl, the lateral wall of which is formed by two tubular parts, 17A and 17B with a circular cross section and by an annular part 18 oriented transversely to the parts 17A and 17B between which it is disposed.

Figure 5:
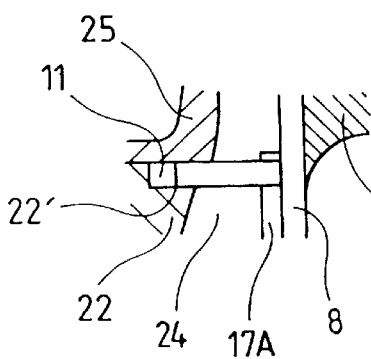
FIG. 5 is a partial elevation view in section showing the cooperation of the lugs on the cartridge with this apparatus.

The internal diameter of the part 17A corresponds to the external diameter of the wall 8 so that the part 17A can be fitted onto the wall 8 with its internal surface in close contact with the external surface of the wall 8. Indentations are formed at the end of the part 17A to enable the lugs 11 to be housed, as can be seen on the right in FIG. 1 and in FIG. 5.

The internal diameter of the part 17B is smaller than that of the part 17A, the internal surfaces of the parts 17A and 17B being connected by an annular surface oriented transversely to the internal surfaces of the parts 17A and 17B, this annular surface being provided by the part 18 and being designed to come into close contact with the end surface of the wall 8 on the same side as the base 6.

A flange 19 with a convex surface on the inside closes off the base 6, this flange being connected transversely to the end of the part 17B opposite to the one by which the latter is connected to the part 18.

When the base 6 is pushed until it comes into abutment on the body 8, that is to say with the lugs 11 housed in the indentations in the part 17A and the part 18 in abutment on the wall 8, there is fluid-tight seal between the body 2 and base 6.

It is also possible to position the cover 6 so that it is no longer the indentations situated at the end of the part 17A which are facing the lugs 11, but the projections situated between the indentations, so that the base 6 is pushed onto the body 2 only as far as a position in which the free end of the projections on the part 17A come to bear on the lugs 11.

In this position, the small slots 20 formed externally in the wall 8 over a certain length as from its free end on the same side as the base 6 are no longer completely masked by the base 6 (the part 17A surrounds the wall 8 over a lesser distance than the length of the slots 20) so that there is communication with the outside by means of the slots 20.

An explanation will now be given how the cartridge is manufactured and how it is sterilized.

First of all, the film 4 is disposed on the corresponding end surface of the wall 8, and then the cover is fitted onto the body 2, which provides a tensioning of the film 4 because the internal surface of the part 12A of the lateral wall of the cover 5 slides over the film beyond the end surface of the wall 8 and therefore tends to drive the film along the external surface of this wall, the film being held, at the end of the fitting-on movement, between the external surface of the wall 8 and the internal surface of the part 12A and between the end surface of the wall 8 and the annular surface which is situated between the internal surfaces of the parts 12A and 12B. By virtue of the small holes 16, any difference in pressure between the two sides of the film 4 liable to deform it is avoided.

The film 4, which is thus tensioned and wedged by the cover 5, is in sealed contact with the wall 8.

The base 6 is then fitted into the position where it is the projections on the parts 17A which come to bear on the lugs 11, that is to say in the position in which the small slots 20 are not completely masked.

The cartridge is then placed in a chamber containing a sterilization gas such as ETO, this gas entering the cartridge through the holes 16 in the cover 5 and through the slots 20 in the wall 8.

Figure 3:
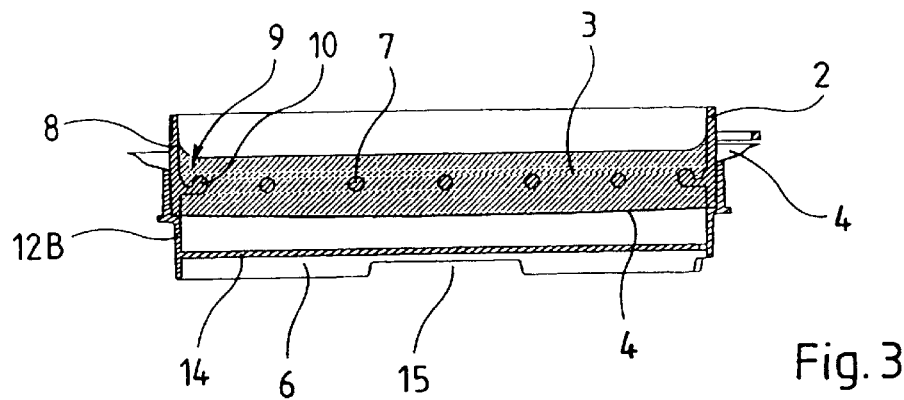
FIG. 3 is an elevation view in section of the cartridge, in the upturned position and without the base.

Once the sterilization has been effected, working under aseptic conditions, the base 6 is removed and the assembly consisting of the body 2, film 4 and cover 5 is turned over and placed on a kind of tripod formed by the portion of the part 12B situated beyond the flange 14, and then growth media, preferably agar, previously heated to make it liquid, is poured into the bowl formed by the body 8 and film 4 until it covers the grid 7, as shown in FIG. 3, and after cooling of the growth media the base 6 is positioned so that the indentations on the part 17A are opposite the lugs 11 and the base 6 is pushed in completely.

The cartridge 1 is then in the configuration shown in FIG. 1. It will be noted that, in this configuration, the layer of growth media 3 is kept completely sterile since it is kept away from any contact with the outside.

Because the ridge 10 on the annulus 9 has no projection on the side facing the film 4, this ridge does not interfere with the filling of the space situated between the film 4 and annulus 9 when the growth media is poured.

The ridge 10, because it projects on the inner side of the annulus 9, remains completely coated by the layer of growth media 3, even if the latter undergoes shrinkage having the effect of separating its periphery from the annular wall 8 of the body 2.

Thus such shrinkage does not cause any break in the fluid-tight seal inside the body 2 between the spaces situated on each side of the layer of the growth media 3.

By virtue of this fluid-tight seal between the inside of the body 2 and the growth media 3 and the one existing between the body 2 and cover 6, the space which faces the end surface of the layer of growth media 3 opposite to the one delimited by the film 4 forms a fluid-tight chamber in which a certain overpressure can exist, as explained below.

Figure 4:
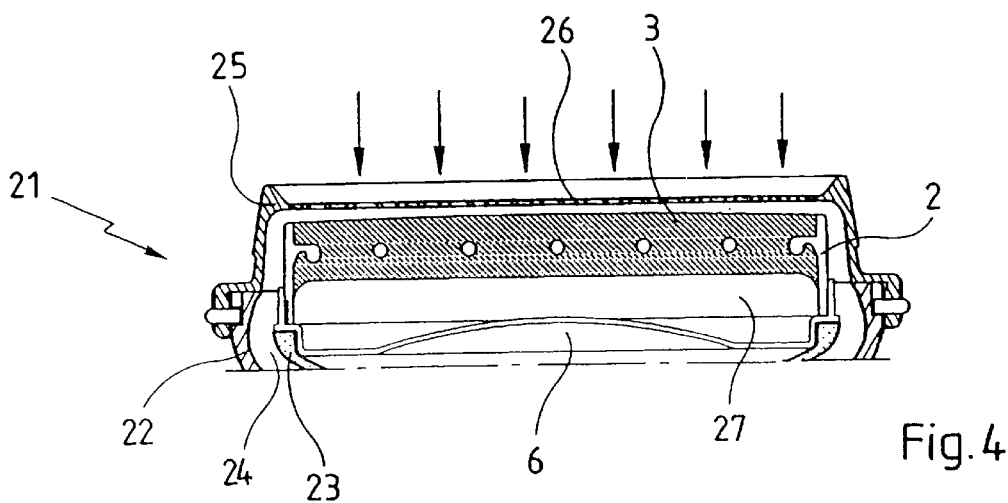
FIG. 4 is an elevation view in section showing this cartridge, the cover and film of which have been removed, fitted in an apparatus for taking an air sample and for the impact on the layer of growth media of the microorganisms present in this sample.
Figure 6:
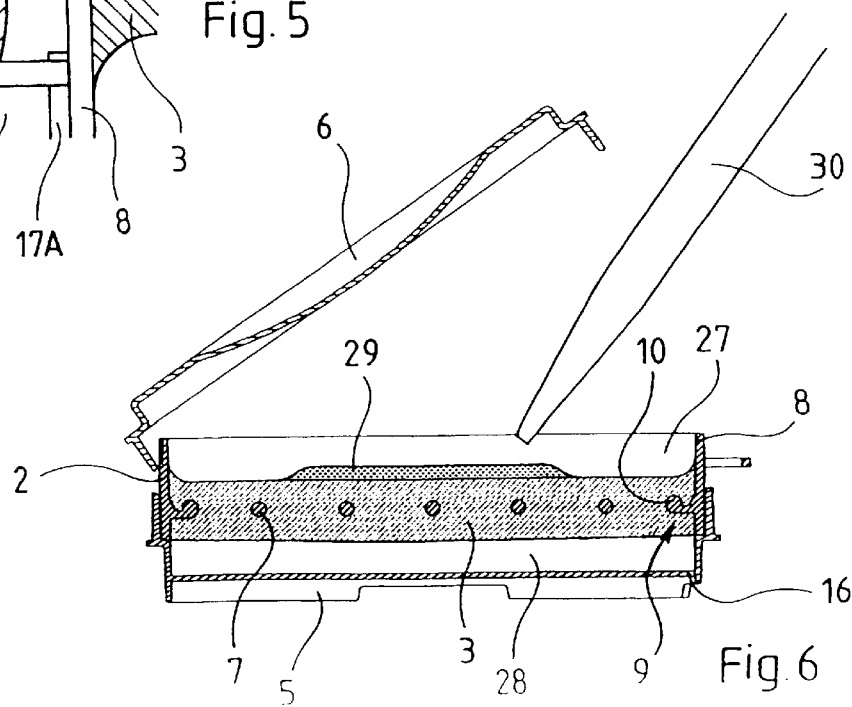
FIG. 6 is an elevation view in section showing this cartridge once again fitted with its cover, in the upturned position, with its base removed in order to deposit a predetermined volume of rehydrating solution on the layer of growth media.

The cartridge 1 has been preferably designed to effect an analysis of a sample of air using the machine 21 shown partially in FIG. 4, which serves to deposit the microorganisms present in the sample of air on the surface of the layer of growth media 3 delimited by the film 4. This device is the subject of co-pending French Patent Application No. 9807299, filed Jun. 10, 1999.

The machine 21 has an aerodynamic sleeve 22 on which a deflector 23 is mounted, so that there exists around the deflector 23 a conduit 24 for the flow of air towards a suction turbine, (not shown).

A removable sieve 25 is mounted on the end of the sleeve 22 which is provided with notches 22' (FIG. 5) in order to receive the end of the lugs of a cartridge 1 whose cover 5 and film 4 have been removed, the sieve 25 having a central wall 26 situated exactly opposite the surface of the layer of growth media 3 which was delimited by the film 4, a multitude of fine perforations being formed in the wall 26.

When the turbine (not shown) of the apparatus 21 operates, the external air is sucked in, as shown by the arrow, through the perforations in the wall 26 and then flows towards the turbine in the conduit 24, the end of the deflector 23 being closed off by the base 6.

The flow of air between the layer of growth media 3 and the wall 26 takes place in the form of a multitude of fine jets each corresponding to a perforation. These air jets strike the layer of growth media 3, the microorganisms present in the air which thus strikes the layer of growth media are affixed on the latter by impaction.

It will be observed that the separation between the layer of growth media 3 and the perforated wall 26 of the sieve 25 has geometric characteristics which are repeated from one cartridge to another, the use of the film 4 for forming the surface of the layer 3 making it possible to fix precisely the positioning of this surface with respect to the body 2, the positioning of the latter with respect to the wall 26 being repeated from one cartridge to another by the fitting of the cartridge on the sleeve 22 by means of the lugs 11 so that, from one cartridge to another, the flow of air sucked in for each rotation of the turbine remains substantially the same, the speed of striking on the layer of growth media 3 consequently remaining constant for the same speed of rotation of the turbine, just as the volume of air sucked in remains constant for the same number of rotations effected by the turbine.

The cooperation between the lugs 11 of the cartridge 1 and their receiving notches 22' situated at the end of the sleeve 22 provides both an axial positioning and a centering of the cartridge 1, only the end of the lugs 11, the free end of which is curved, being received in the notches.

The lugs 11 are then disposed across the conduit 24, but the perforations, in the example shown three in number, which are formed therein, allow passage of air to the turbine.

The cooperation between the cartridge 1 and the deflector 23 takes place with a certain amount of clearance, sufficient to close off the deflector, the cover 6 being fitted thereon internally, the external diameter of the part 17B being smaller than the internal diameter of the end of the deflector 23.

Once the required volume of air has been sucked in, the sieve 25 is removed from the machine 21, the cover is fitted in place again on the cartridge 1 and the latter is retrieved.

All that remains to be carried out, in a conventional fashion, is the culturing of the microorganisms impacted on the layer 3, by placing the cartridge in an incubator heated to a predetermined temperature such as 32.5° C. (+/−2.5° C.) for the required time, for example two days, the cartridge 1, by virtue of the holes 16 in the cover 5, allowing the gaseous exchanges, notably aerobic, necessary to the development of the colonies.

The cartridge 1 is preferably turned over to effect the culturing, being placed on the kind of tripod formed by the portion of the part 12B of the lateral wall which extends beyond the flange 14, the indentations 15 allowing the circulation of air. The fact that the flange 14 is situated underneath the layer of growth media 3 (and not on top) preventing, in a well-known fashion, the phenomena of condensation on the cover.

The space 27 delimited by the layer of growth media 3, the wall 8 and the base 6 forming a fluid-tight chamber, the air that is contained therein was put under slight overpressure when the base 6 was closed, and furthermore an additional overpressure will be created because this air expands when it takes the temperature of the incubator, which is in principle higher than the initial temperature of this volume of air.

The space 28 delimited by the layer of growth media 3, the wall 8 and the cover 5 being in communication with the outside, notably through the holes 16, there exists, because of the overpressure in the chamber 27, a pressure difference between the two end surfaces of the layer of growth media. This pressure difference assists the rehomogenization of the layer of growth media 3, in particular at the surface that was impacted in the machine 21.

As a matter of fact, the air jets which struck this surface of the layer of growth media 3 formed craters therein and caused a certain amount of drying which reduces the nutritive capabilities thereof.

This drying is relatively great: it is estimated for example that it is usual to lose 2 g of water for a sampled air volume of 1 $m^3$ out of a total of 34 g for the layer of growth media 3.

It is possible, rather than relying solely on the water remaining in the layer of growth media 3 for rehydrating the impacted surface, to deposit a certain volume of rehydrating solution 29 on the layer 3, on the opposite side to the impacted surface, as shown in FIG. 6.

To carry out this deposition, the base 6 is removed and, using a pipette 30, the required volume of rehydrating solution 29, which corresponds for example to 80 or 90% of the dehydration established by weighing the cartridge 1, is deposited.

The rehydrating solution will reach as far as the opposite surface of the layer 3 by virtue of gravity, but also and particularly by virtue of the overpressure in the fluid-tight chamber, which assists the diffusion of liquid, and notably of the solution 29, in the layer 3.

The rehydration of the impacted surface will cause the craters to disappear, which is beneficial to the development of the colonies and therefore facilitates their identification, the fact that the surface is smooth also assisting counting, and also the subculturing of the colonies requiring specific identification.

According to the circumstances, the rehydrating solution contains only water or water mixed with nutritional substances and/or specific dyes permitting selective identification or growth of the microorganisms impacted on the layer of growth media.

It will be noted that the square shape of the meshes of the grid 7 advantageously gives the user an indication of the size of the surface on which the colonies have developed, each mesh delimiting for example a surface area of 1 cm. The growth media being transparent, it is preferable for the grid 7 to be colored in order to be easily visible, the body 2 being for example molded from a black plastic. The cover 5 is transparent so that reading can be effected whilst the cartridge 1 remains closed.

It is of course understood that the cartridge according to the invention can be used for other types of analyses, for example in order to determine the contamination of a liquid, the surface of the layer of growth media 3 which is delimited initially by the film 4 receiving a membrane through which the required volume of liquid to be analyzed is passed.

Numerous variants are possible according to circumstances, and it should be stated in this regard that the invention is not limited to the examples described and depicted.

What I claim:

1. A cartridge for culturing microorganisms comprising a cartridge having a body with a grid and an annular wall oriented transversely to said grid and surrounding it, and having a layer of growth media oriented parallel to said grid and coating it; a flexible fluid-tight film tensioned over an end surface of the annular wall and delimiting an end surface of said layer of growth media, a removable cover adapted to wedge said film between the external surface of said annular wall and an internal surface of a lateral wall of said cover and a removable base adapted to fit onto said body opposite said film.

2. The cartridge according to claim 1, wherein said cover is also adapted to wedge said film between said end surface of said annular wall of the body and a second internal surface of said cover.

3. The cartridge according to claim 1, wherein said cover has a closure flange disposed at a distance from said film when said second internal surface of the lateral wall of the cover wedges said film against said end surface of said annular wall of the body.

4. The cartridge according to claim 1, wherein said cover has at least one hole allowing communication between the inside and outside of the cover when the latter is fitted onto said body.

5. The cartridge according to claim 2 wherein said body and said cover are each made from molded plastic, said cover being more flexible than said body.

6. The cartridge according to claim 2 wherein said body and said cover are each made from molded plastic, said cover being more flexible than said body.

7. The cartridge according to claim 3 wherein said body and said cover are each made from molded plastic, said cover being more flexible than said body.

8. The cartridge according to claim 4 wherein said body and said cover are each made from molded plastic, said cover being more flexible than said body.

9. The cartridge according to claim 1 wherein the removable base delimits a fluid-tight chamber, onto which gives the end surface of said layer of growth media that is opposite to the one delimited by said film.

10. The cartridge according to claim 1 wherein the removable base delimits a fluid-tight chamber, onto which gives the end surface of said layer of growth media that is opposite to the one delimited by said film and said base fits externally onto said annular wall of said body and has an internal surface coming into contact with the end surface of said annular wall situated on the same side as the base.

11. The cartridge according to either claim 9 or 10, wherein said body and said base is made from molded plastic, said base being more flexible than said body.

12. The cartridge according to claim 1 wherein said body has, between said annular wall and said grid, a solid annulus having towards the inside an extra thickness part forming a ridge.

13. The cartridge according to claim 1 wherein said body has, between said annular wall and said grid, a solid annulus having towards the inside an extra thickness part forming a ridge and said annulus has no projection on the side facing the film.

14. The cartridge according to claim 1 wherein said grid is in a color contrasting with said layer of growth media.

15. A method of air analysis for microorganisms comprising the use of a cartridge according to claim 1, with a step of striking with air jets said end surface of the layer of growth media delimited initially by said film.

16. The method according to claim 15 further comprising after said striking step, a step of depositing a predetermined volume of rehydrating solution on the end surface of said layer of growth media opposite to the one delimited initially by said film.

17. The method according to claim 15 wherein said step of depositing a predetermined volume of rehydrating solution is performed with said cartridge turned over.

18. An air analysis apparatus having a removable sieve with a wall in which there are formed a multitude of fine perforations each forming an air jet striking a surface of a layer of growth media in a receptacle fitted in said apparatus, characterized in that said receptacle is formed by a cartridge according to claim 1, the struck surface being the end surface of the layer of growth media initially delimited by said film, and in that said apparatus has a positioning support common to said sieve and to the body of said cartridge.

19. The apparatus according to claim 18 wherein said support has notches for housing the end of external lugs on said body.

20. The apparatus according to claim 19 wherein said lugs are perforated.

* * * * *